ized Patent number: US 7,415,882 B2

(12) United States Patent
Fetzer et al.

(10) Patent No.: US 7,415,882 B2
(45) Date of Patent: Aug. 26, 2008

(54) METHODS AND SYSTEMS FOR INSPECTION OF COMPOSITE ASSEMBLIES

(75) Inventors: Barry A. Fetzer, Renton, WA (US); Fred D. Young, Bellevue, WA (US); Hien T. Bui, Auburn, WA (US); Michael J. Duncan, Sumner, WA (US); Mark A. Lee, Kent, WA (US)

(73) Assignee: The Boeing Company, Irvine, CA (US)

( * ) Notice: Subject to any disclaimer, the term of this patent is extended or adjusted under 35 U.S.C. 154(b) by 294 days.

(21) Appl. No.: 11/311,797

(22) Filed: Dec. 19, 2005

(65) Prior Publication Data
US 2007/0137302 A1 Jun. 21, 2007

(51) Int. Cl.
*G01N 9/24* (2006.01)
(52) U.S. Cl. .......................................... 73/634
(58) Field of Classification Search ............ 73/632–634
See application file for complete search history.

(56) References Cited

U.S. PATENT DOCUMENTS

| | | | | |
|---|---|---|---|---|
| 3,534,591 A * | 10/1970 | Phelan | ........................ | 73/634 |
| 3,575,043 A * | 4/1971 | Allen et al. | .................... | 73/619 |
| 3,858,437 A * | 1/1975 | Jarzynski et al. | .............. | 73/597 |
| 3,898,838 A * | 8/1975 | Connelly | ...................... | 73/634 |
| 4,311,556 A * | 1/1982 | Iwamoto et al. | ............. | 376/249 |
| 4,351,006 A | 9/1982 | Clough et al. | .................. | 386/84 |
| 4,452,753 A | 6/1984 | Wentzell et al. | ............. | 376/249 |
| 4,532,807 A * | 8/1985 | Tomita et al. | .................. | 73/602 |
| 4,881,177 A * | 11/1989 | McClean et al. | ............ | 700/258 |
| 5,031,458 A | 7/1991 | Young et al. | ................... | 73/634 |
| 5,585,564 A | 12/1996 | Brunty et al. | .................. | 73/634 |
| 5,698,787 A * | 12/1997 | Parzuchowski et al. | ....... | 73/643 |
| 6,131,460 A | 10/2000 | Brunty et al. | ................. | 73/634 |
| 6,167,760 B1 | 1/2001 | Brunty et al. | ................. | 73/634 |
| 6,234,024 B1 | 5/2001 | Brunty et al. | ................. | 73/634 |
| 6,698,291 B2 | 3/2004 | Yamamoto et al. | ............ | 73/620 |
| 6,848,312 B2 * | 2/2005 | Georgeson | ................... | 73/627 |

\* cited by examiner

*Primary Examiner*—Hezron E. Williams
*Assistant Examiner*—Tamiko D Bellamy
(74) *Attorney, Agent, or Firm*—Armstrong Teasdale LLP (57) ABSTRACT

An apparatus for the ultrasonic testing of internal areas of prefabricated composite assemblies as described. The composite assemblies have one or more internal areas formed therein. The apparatus includes at least one receive transducer, at least one transmit transducer, a vertical member, a support member slidably attached to the vertical member, a pair of substantially parallel hollow rods, and an ultrasonic testing system. Each rod comprises a transducer attachment end with receive transducers attached to the transducer attachment end of a first rod, and transmit transducers attached to the transducer attachment end of a second rod. The rods are slidably attached to the support member and manually movable with respect to a composite assembly to be tested. The ultrasonic testing system is coupled to the receive transducers through the first rod, and coupled to the transmit transducers through the second rod.

25 Claims, 5 Drawing Sheets

METHODS AND SYSTEMS FOR INSPECTION OF COMPOSITE ASSEMBLIES

BACKGROUND OF THE INVENTION

This invention relates generally to ultrasonic inspection of composite assemblies and more specifically, to methods and systems for inspection of composite assemblies that may include cavities.

More and more structures are fabricated utilizing composite materials. For example, airframes currently being developed incorporate more composite parts than previous airframes. However, utilization of more composite parts results in additional requirements for ultrasonic inspection to provide information with regard to the integrity of these additional composite parts.

Most facilities that fabricate composite materials, and thus composite parts, have limited capabilities for providing a fast, thorough ultrasonic inspection of these composite parts. One example of such a composite part is a movable trailing edge wing component. Traditionally, such a part was fabricated from metallic materials. In new generation aircraft, this component will be fabricated from composite material. As such, ultrasonic inspection will need to be utilized for this component, and the information provided by such an ultrasonic inspection will be utilized in the manufacturing process. Specifically, the ultrasonic inspection information will be utilized in adjusting the manufacturing process to ensure that quality parts are being produced for such an airframe component.

At least some composite components will be fabricated to include deep recessed cavities, for example, up to 30 inches deep. These cavities limit current ultrasonic technologies from performing a fast and thorough inspection. While computer controlled, gantry based, ultrasonic inspection systems are known to exist, for many inspection applications, such systems are prohibitively expensive to implement, and may not include flexibility for the inspection of many different composite assemblies.

BRIEF DESCRIPTION OF THE INVENTION

In one aspect, an apparatus for the ultrasonic testing of internal areas of prefabricated composite assemblies is provided. The apparatus includes at least one receive transducer, at least one transmit transducer, a vertical member, a support member slidably attached to the vertical member, and a pair of substantially parallel hollow rods. Each rod includes a transducer attachment end. The receive transducer is attached to the transducer attachment end of a first rod, and the transmit transducer is attached to the transducer attachment end of a second rod. The rods are slidably attached to the support member and manually movable with respect to a composite assembly to be tested. The apparatus further includes an ultrasonic testing system coupled to the receive transducer through the first rod, and the ultrasonic testing system is coupled to the transmit transducer through the second rod.

In another aspect, a method for operator controlled ultrasonic inspection of prefabricated composite assemblies is provided. The method includes engaging the assembly to be inspected with transmit and receive transducers, the transmit and receive transducers mounted opposite one another on substantially parallel rods, the portion of the assembly to be inspected in the space between the transmit transducers and the receive transducers. The method further includes outputting ultrasonic inspection signals from the transmit transducers, receiving the ultrasonic inspection signals at the receive transducers, providing for planar, operator assisted movement of the rods during the outputting and receiving steps, and analyzing the signals received at the receive transducers to determine a condition of the assembly being inspected.

In still another aspect, a device enabling operator assisted ultrasonic inspection of composite assemblies is provided. The device includes a vertical member, a support bracket slidably attached to the vertical member, an air cylinder attached to the support bracket and the vertical member, a pair of rods slidably attached to the support bracket and substantially perpendicular to the vertical member, and transmit and receive transducers. The air cylinder is configured for operator assisted movement of the support bracket with respect to the vertical member. The pair of rods are slidably attached to the support bracket and substantially perpendicular to the vertical member. The rods are manually movable with respect to the support bracket, and each rod includes a transducer attachment end. The transmit and receive transducers are mounted to respective transducer attachment ends and are oriented such that a composite assembly may be inserted into a space between the transmit transducers and the receive transducers and between the rods.

DETAILED DESCRIPTION OF THE INVENTION

Herein described is a rapid inspection technique and system that can protrude deep into the cavities of a composite component, for example, a movable trailing edge wing component to instantly provide a user with C-scan data resulting from the inspection of the composite component. Inspection of such components is facilitates the manufacture and production of both the herein described composite component and other composite components that also may include cavities.

The described inspection system provides the ability to rapidly inspect large recessed composite areas without the added complexity of motion control hardware and software. Specifically, the system is operated manually with the aid of air cylinders. The air cylinders minimize the exerted force necessary for a user to apply to accurately control placement of transmit and receive transducers. The air cylinders help to control movement of the transducers by countering the effects of gravity. Therefore, the operator/user can make directional changes for the transmit and receive transducers with little applied force, for example, three pounds of force. The small amount of applied force required of a user provides for a manual ultrasonic inspection with minimal impact on the human operator. As further described herein, adjustments that can be made with respect to a pedestal also provide a safe ergonomic operating zone that can be easily adjusted for a wide variety of inspection locations and operator variables, for example, the height of an operator.

The use of fast, multi-channel ultrasonic electronics and positional feedback to a computer system having a visual user interface, provides the operator with the ability to see the inspection results at updating rates in excess of seven square inches/second. An analogy is the operator painting a picture of the part under inspection on the computer screen as they are moved rods up and down, and back and forth, with minimal effort. Easy manual manipulation of the transmit and receive transducers eliminates the need for motors, motion control hardware and software, while still maintaining a respectable inspection speed and area coverage.

Figure 1:
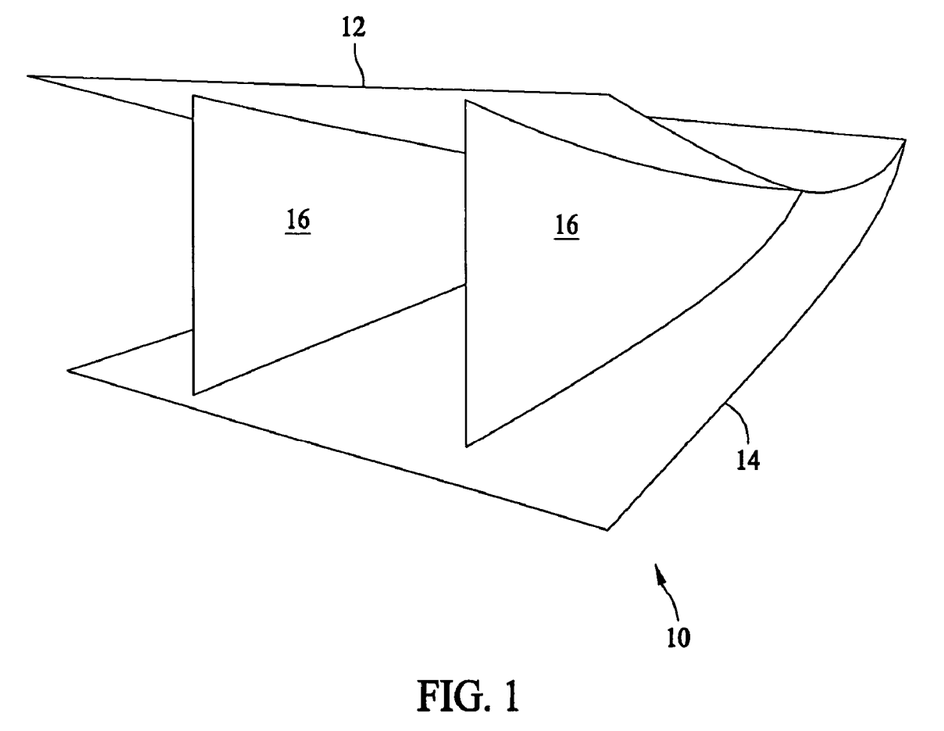
FIG. 1 is a diagram illustrating a movable trailing edge wing component fabricated from composite materials and having one or more deep cavities formed therein.

FIG. 1 is a diagram of a movable trailing edge wing component 10. Wing component 10 includes an underside 12, a top surface 14, and a plurality of web components 16 that extended between and are affixed to underside 12 and top surface 14. Web components 16 are substantially perpendicular to the respective underside 12 and top surface 14 at the locations where web components 16 are affixed. Web components 16 provide stability and strength to wing component 10 and help to maintain relative positioning between underside 12 and top surface 14 of wing component 10. In the production of wing component 10, web components 16 need to be inspected. One system for inspecting of composite components is an ultrasonic inspection system. An ultrasonic inspection system provides a C-scan image on a computer screen as a user is taking ultrasonic data with the inspection system.

Figure 2:
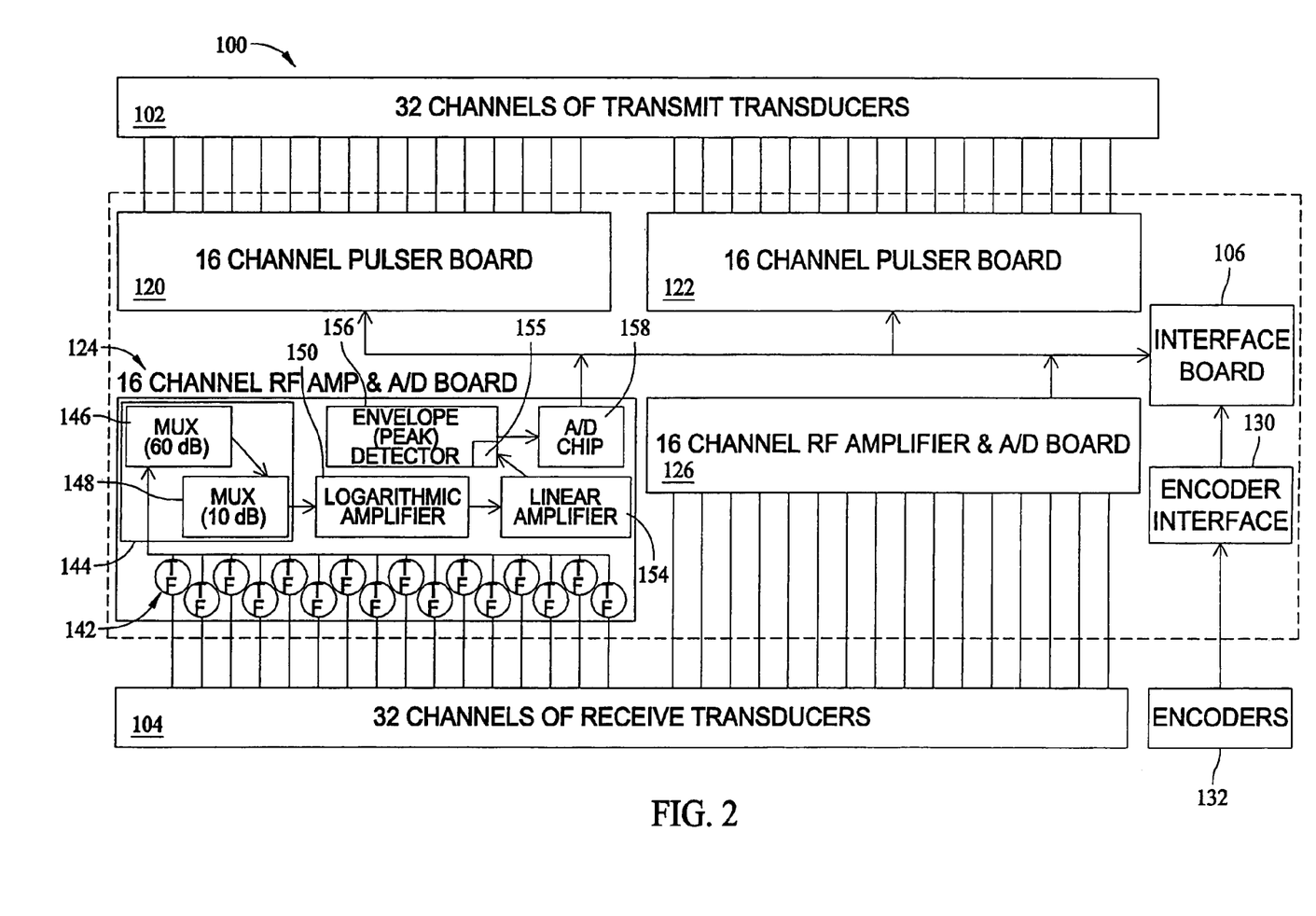
FIG. 2 is a schematic block diagram of a multi-channel, multiplexed, through-transmission ultrasonic inspection system.

FIG. 2 is a schematic block diagram of one embodiment of an ultrasonic inspection system 100. Ultrasonic inspection system 100 is a thirty-two channel multiplexed through-transmission ultrasonic (TTU) inspection system. Specifically, system 100 includes thirty-two pairs of corresponding transducers. Of the sixty-four transducers, thirty-two transducers are transmitting transducers 102 or pulsing transducers on one side of a component or structure (for example, wing component 10 shown in FIG. 1) under inspection. The other thirty-two transducers are receiving transducers 104 on the opposing side of the structure under inspection. Thus, thirty-two channels are provided for thirty-two transmit transducers 102 and thirty-two channels are provided for thirty-two receive transducers 104. As used herein, a "channel" refers to the communication link to a transducer. The transducers may be included in one device or probe. Alternatively, the plurality of channels may be divided in such a manner as to function as an array of probes, such as a sixty-four probe array with thirty-two transmitting probes and thirty-two receiving probes, where each probe includes one transducer. Each transmit or receive channel corresponds with an individual piezoelectric crystal transducer. The individual transducers, as described, may be arranged as in a single probe or a number of probes functioning in an array.

Each of the thirty-two transmit channels 102 may be sequentially pulsed, such as a pulser board pulsing channels 1 through thirty-two, one channel every 200 microseconds (us), at a 5 kHz repetition rate to cycle through the thirty-two channels 102 once every 6.4 milliseconds (ms). A pulser board pulsing channels refers to the pulser board providing a transmit signal to a transmit channel for a transducer. An example pulser board, or interface board or receiver board, may be a printed circuit board (PCB) with electrical connections or communication paths. An interface board 106, and/or a processor or microcontroller of an attached computer (not shown), may be used to control the sequential pulsing of the thirty-two transmit channels 102 and coordination of the sequence of received signals. The repetition rate for the cycling of channels is typically selected, and limited, in part due to the time for an ultrasonic signal to propagate from a transmitting transducer crystal through a couplant to the surface of the part, through the part under inspection, and from the surface of the part through a couplant to a receiving transducer crystal. The repetition rate may also be dependent upon such factors as the communication bandwidth to transmit the processed signals from the multiplexing receiver board to a computer controlling and/or processing the inspection.

The embodiment illustrated in FIG. 2 shows two sixteen channel pulser boards 120, 122, each connected to an interface board 106 and each providing sixteen of the thirty-two transmit channels 102. A pulser board typically is a PCB board which can independently provide signals intended for the sixteen different transducers from an interface board to the sixteen corresponding channels using corresponding pulsers of the pulser board. The corresponding pulsers provide electronic pulse signals for the digital or electronic signals from the interface board. Also included are two sixteen channel receiver boards or RF amplifier and A/D boards 124, 126, each coupled to the interface board 106 and each receiving sixteen of the thirty-two receive channels 104.

A thirty-two channel multiplexed TTU system as shown in FIG. 2 may also include an encoder interface 130 to provide an interface between positional encoders 1thirty-two of a scanning system and an interface board 106 of the thirty-two channel multiplexed TTU system. An encoder interface 130 may include two counter chips, such as L87266R1 counter chips manufactured by LSI Computer Systems, Inc., of Melville, N.Y. The counter chips have internal registers which hold the current value as an encoder on the scanning system moves back and forth with a scanning probe. The counter chips will count up and down from a reference value to provide different values for the internal registers of the counter chips. Such information is typically referred to as position information of the scanning system. The position information is relative to the position of the transducers in some physical manner because the encoders are mechanically tracking the movement of the transducers. Thus, the position information provided by an encoder is synchronous to the movement of a scanning probe, but the transducer signals are asynchronous to the scanner movement. Thus by combining the position information of the encoder through an encoder interface, a microprocessor is capable of tying the two pieces of information together to establish the position of a transducer for a particular ultrasonic signal. For example, a microprocessor may combine positional information from the counter chips of the encoder interface into the same data packet as the corresponding ultrasonic data. Additional software may then be able to analyze the particular data packet as having an ultrasonic data value at a specific position which occurred during the scan. Although encoders are typically used to provide position information, encoders may additionally or alternatively be used to provide such data as speed data, velocity data, and distance data.

A receiver board 124, 126 may include a tuned filter 142 for each receive channel 104. For example, a tuned filter 142 may include a base amplifier and a tank circuit. A tunable capacitor of a tuned filter 142 may be adjusted to filter the received signal to a specific frequency, such the frequency of a piezoelectric crystal oscillating at 5 MHz. After filtering each of the received signals, all sixteen signals are provided to a first layer of multiplexing switches 146, referred to as a first multiplexing chip. As a non-limiting example, a multiplexing chip may be a MAX310CPE multiplexing chip manufactured by Maxim Integrated Products, Inc., of Sunnyvale, Calif., which permits a signal voltage input range of 15 volts peak-to-peak (Vpp). The first layer of multiplexing switches 146 may provide 60 dB of isolation between the sixteen signals. A second layer of multiplexing switches 148, also referred to as a second multiplexing switch may provide an additional 10 dB of isolation between the channels. The second layer of multiplexing switches 148 may also use MAX3I OCPE multiplexing switches. Using two layers of multiplexing switches 148 can achieve 70 dB) of isolation between the channels. With 70 dB of isolation between channels, one channel can be 3000 times greater than another channel without affecting the smaller input as provided by 70 dB=20×Log (difference) where (difference) is equal to 3000 for 70 dB. For example, one channel can have a 5 MHz signal with a strength of one millivolt (mV) and another channel can have a 5 MHz signal with a three volt (V) strength without affecting the 1 mV signal. Also, by separating the multiplexing switches into two layers, the capacitance is decreased so as not to degrade the RF signal. Different combinations of channel switching may be used with the two layers of multiplexing switches. For example, a single 60 dB multiplexing chip used to switch between sixteen channels may be used with two 10 dB multiplexing chips to switch between eight channels each. By selecting corresponding channels in the first layer of multiplexing switches 146 and the second layer of multiplexing switches 148, a single receive channel may be selected.

The single receive channel signal, filtered and multiplexed, is provided to a logarithmic amplifier 150 which provides logarithmic amplification for 70 dB of dynamic range, such as a voltage range of −67 dB to +3 dB, although logarithmic amplification can be centered around different dynamic ranges. Thus, the layered multiplexing chips 146, 148 provide the fill dynamic range of the capabilities of the logarithmic amplifier 150. Logarithmic amplification follows the formula $Gain_{log}=20 \times Log(V_{out}/V_{in})$. After logarithmic amplification, the signal may be linearly amplified by a linear amplifier 154, such as to provide 20 dB of linear amplification to adjust the logarithmically amplified signal to the full range of an analog to digital converter. Linear amplification follows the formula $Gain_{lin}=(V_{out}/V_{in})$. The signal may then be converted from analog to digital using an analog to digital chip 158 (A/D converter), such as an analog to digital converter with an input range of 0 to 10 volts. An envelope (peak) detector 156 and a diode 155 may be used between the linear amplification and the conversion from analog to digital such that the peak value is converted to a digital signal by the A/D converter. The diode 155 can isolate the positive voltage of the amplified signal to permit the envelope (peak) detector 156 to capture the peak amplitude of the signal. Only the peak amplitudes of a signal are required for TTU inspection to identify flaws from changing amplitudes. For example, the logarithmic amplifier 150 may output a signal with 1.4 volts peak-to-peak (Vpp) centered around 0 volts; the linear amplifier 154 may increase the signal to a 20 Vpp signal (−10 V to +10 V); the diode 155 may isolate the +10 V peak range (0 V to +10 V); the envelope peak detector 156 may capture the peak amplitudes of the signal ranging from 0 V to +10 V; and the analog to digital chip 158 may convert the 0 V to 10 V signal to a digital signal with a 12 bit resolution.

The use of the large 70 dB dynamic range logarithmic amplification assists in the identification of small changes or imperfections in a part under inspection. For example, 70 dB of dynamic range maybe required to find a piece of foreign material located 68 plys (layers) into a half inch thick piece of graphite composite material under inspection, where one ply, or one layer, is seven thousandths of an inch thick. The foreign piece of material may be almost on the bottom edge of the piece of graphite under inspection as viewed through the part from the transmitting transducer to the receiving transducer. Sound, or specifically an ultrasonic signal, diminishes as it propagates through a part under inspection.

For example, in the inspection of the half inch thick piece of graphite, the ultrasonic signal may have dropped by as much as 60 dB in through transmission before it reaches the $68^{th}$ ply where the piece of foreign material is located and for which 2 dB of change may be necessary to detect the presence of the piece of foreign material. In order to detect the 2 dB of change, the noise must not be so great as to mask the 2 dB change for the piece of foreign material. The dynamic range must be large enough to detect the flaw in the structure under inspection, the piece of foreign material in the graphite. By using a large logarithmic gain, a scanning system may be capable of resolving a high level of detail in a part under inspection. Using logarithmic amplification amplifies the small changes more than large changes in the signal. Typically, large changes in a signal include noise. By comparison, when using linear amplification, the noise is amplified just as much as the signal. And by using a large dynamic range, a system is capable of scanning thick parts.

In addition to accounting for a high dynamic range, the system 100 multiplexes the high dynamic range without acquiring crosstalk, or noise between the channels. In order to switch or multiplex the large dynamic range signals without introducing noise or crosstalk between the channels, the multiplexing may be performed by layering multiplexing chips, such as described by using an initial 60 dB range and a second layer of 10 dB range multiplexing chips.

Figure 3:
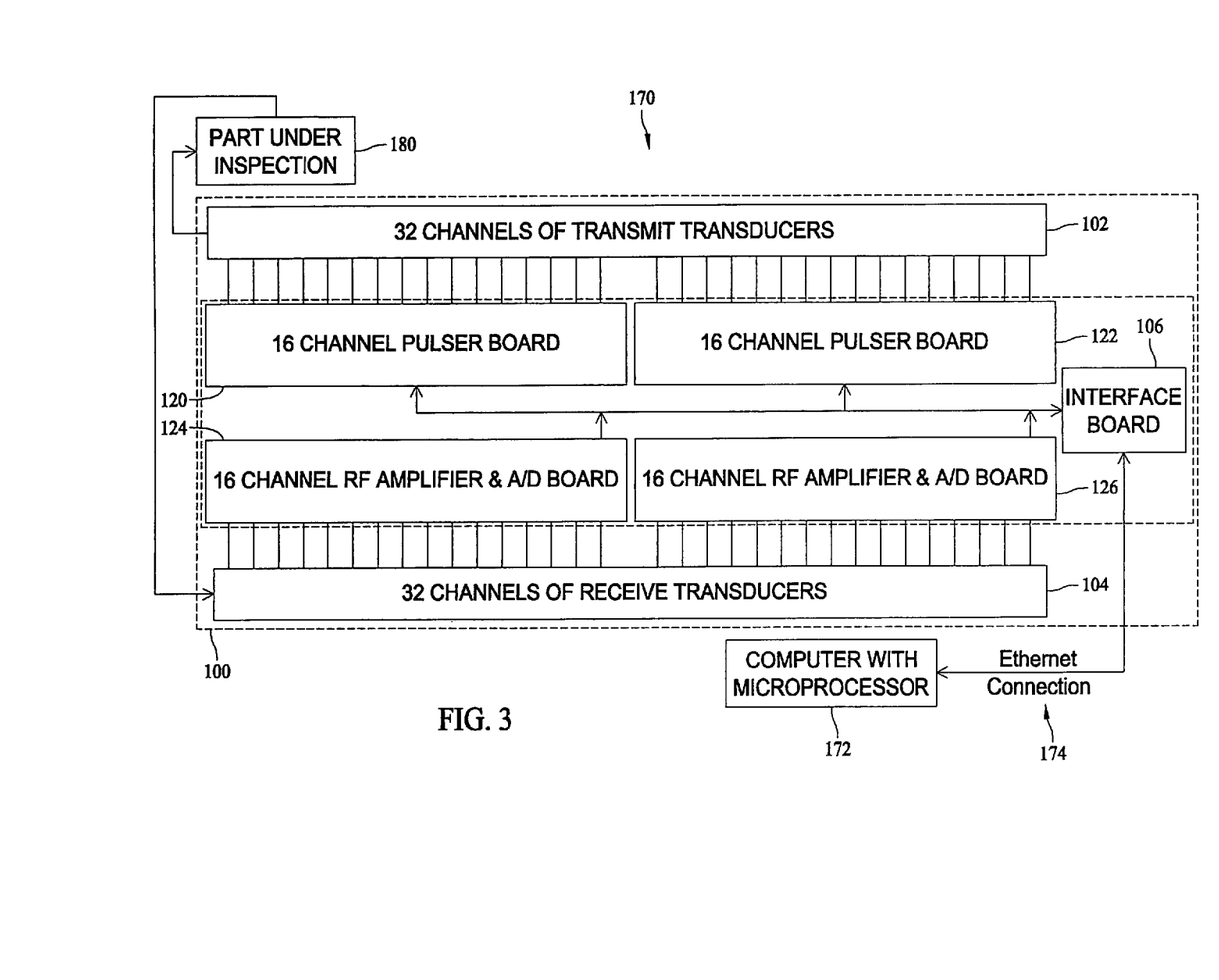
FIG. 3 is a schematic block diagram of a multi-channel, multiplexed, through-transmission ultrasonic inspection system connected to a remote processor using an Ethernet connection.

FIG. 3 is a schematic block diagram 170 of a thirty-two channel multiplexed through-transmission ultrasonic inspection system 100 connected to a remote processor 172 using an Ethernet connection 174. As illustrated in FIG. 3, thirty-two transmit channels 102 may be coupled to thirty-two transducers which are used to inspect a part 180. thirty-two receive channels 104 may be coupled to thirty-two receive transducers to receive signals transmitted through a part under inspection 180 from thirty-two corresponding transmitting transducers. The multiplexed through-transmission ultrasonic inspection system may be connected to a remote processor 182, such as a computer with a microprocessor for further processing, analyzing, and displaying results of the inspection, through a communication connection or a link, such as Ethernet connection 174 or a serial communication connection.

The above described ultrasonic inspection system 100, while electrically configured for the ultrasonic testing of composite materials such as graphite composites, has mechanical limitations. Specifically, known mechanical mounting configurations of transducers 102 and 104 include prohibitively expensive gantry-based systems that may be best utilized in the inspection of large sheets of such material. Therefore, ultrasonic inspection system 100 has not been utilized for the inspection of three-dimensional assemblies fabricated from composite materials, such as, wing component 10 (shown FIG. 1).

Figure 4:
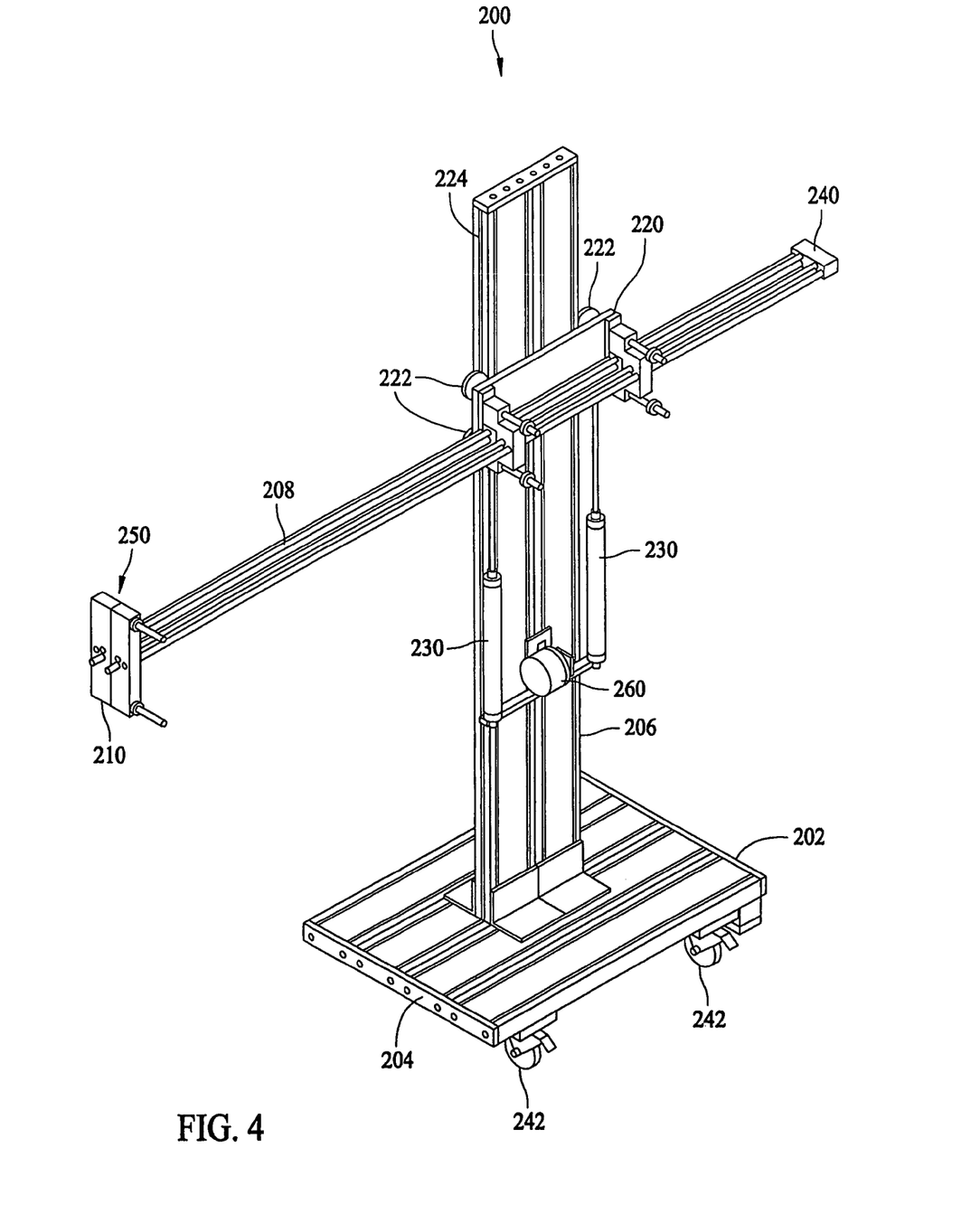
FIG. 4 is a plan view of a mechanical device for the attachment of transducers which allow for the through-transmission ultrasonic inspection of composite assemblies that include one or more deep cavities.

FIG. 4 is a plan view of a mechanical device 200 which provides for ultrasonic inspection of composite assemblies that include one or more deep cavities. Mechanical device 200 includes a pedestal frame 202 having a horizontal base 204 and a vertical member 206 extending vertically therefrom. Coupled to vertical member 206 are a plurality of movable rods 208 having multiple channel ultrasonic inspection probes 210 mounted thereon providing a capability to reach into cavities of preassembled parts allowing for their ultrasonic inspection. The probe and rod assembly provides a user with the capability of quickly inspecting internal areas of composite assemblies by pushing rods 208 back and forth and up and down into cavities formed by pre-assembled composite assemblies.

Inspection probes 210 form a part of, and are electrically connected to, a system, for example, ultrasonic inspection system 100 (shown in FIG. 2). As described above, ultrasonic inspection system 100 includes ultrasonic testing electronics and software that provide a C-scan image on a computer screen as a user is utilizing system 100 along with mechanical device 200 to gather ultrasonic test data. By this manner, the user can inspect the internal web 16, for example, of a wing component 10 (shown in FIG. 1) in roughly one minute.

Referring still to FIG. 4, attached to vertical member 206 is a movable supporting bracket 220. Movable supporting bracket 220 moves up and down to vertical member 206 by use of wheels 222 attached to movable supporting bracket 220. Wheels 222 are run inside a grooved notch 224 in vertical member 206. Air cylinders 230 are attached to the movable support bracket 220 and also vertical member 206. Air cylinders 230 provide for easy movement of the support bracket by a user in the up and down direction and also counter the effects of gravity to allow a user to easily move rods 208 in a back-and-forth direction. In this manner, air cylinders 230 provide up and down movement with very little externally applied force in either direction needed from a user.

Movable rods 208 slide back and forth through supporting bracket 220. Movable rods 208 have a handle 240 on one end and the inspection probes 210 on the other end. The user manipulates the location of inspection probe 210 by moving handle 240 back and forth and movable supporting bracket 220 up and down. The pedestal frame 204 has wheels 242 to provide portability and also has the ability to lock in place during an inspection. In one embodiment, inspection probes 210, are through-transmission ultrasonic inspection probes. Therefore, inspection probes 210 include the two halves, transmit transducers and receive transducers, and the composite part to be inspected is inserted in between the two halves at slot 250. Transmit transducers of inspection probe 210 are mounted on a first of movable rod 208, and receive transducers are mounted on a second of movable rods 208. In one embodiment, magnets are utilized in the inspection probe halves to keep the halves of the probe aligned properly. In an embodiment which utilizes a pulse echo testing methods, a single rod 208 is utilized to which both transmit and receive transducers are mounted, enabling testing of an assembly from a single surface.

One or more encoders 260 (similar to encoders 1 thirty-two shown in FIG. 2) are mounted on vertical member 206. Encoders 260 keep track of the position of the inspection probes 210 by electronically providing pulses to through-transmission ultrasonic inspection system 100 when rods 208 move with respect to support bracket 220 or support bracket 220 moves with respect to vertical member 206. If rods 208 are moved, encoders 260 are used to monitor movement back or forth (X direction) and send electronic pulses indicative of movement in the X direction. If support bracket 220 moves up or down, encoders 260 are used to monitor this movement (Y movement) and send electronic pulses indicative of movement in the Y direction. Through-transmission ultrasonic inspection system 100, as described above, includes counters that keep track of the electronic pulses and provide count information to the system software as directional information that is required for C-scan ultrasonic testing and inspection.

The system software receives ultrasonic test data and positional data from inspection system 100 electronics. This ultrasonic test data is mapped real time to an X & Y C-scan image for the user to view on a monitor.

Figure 5:
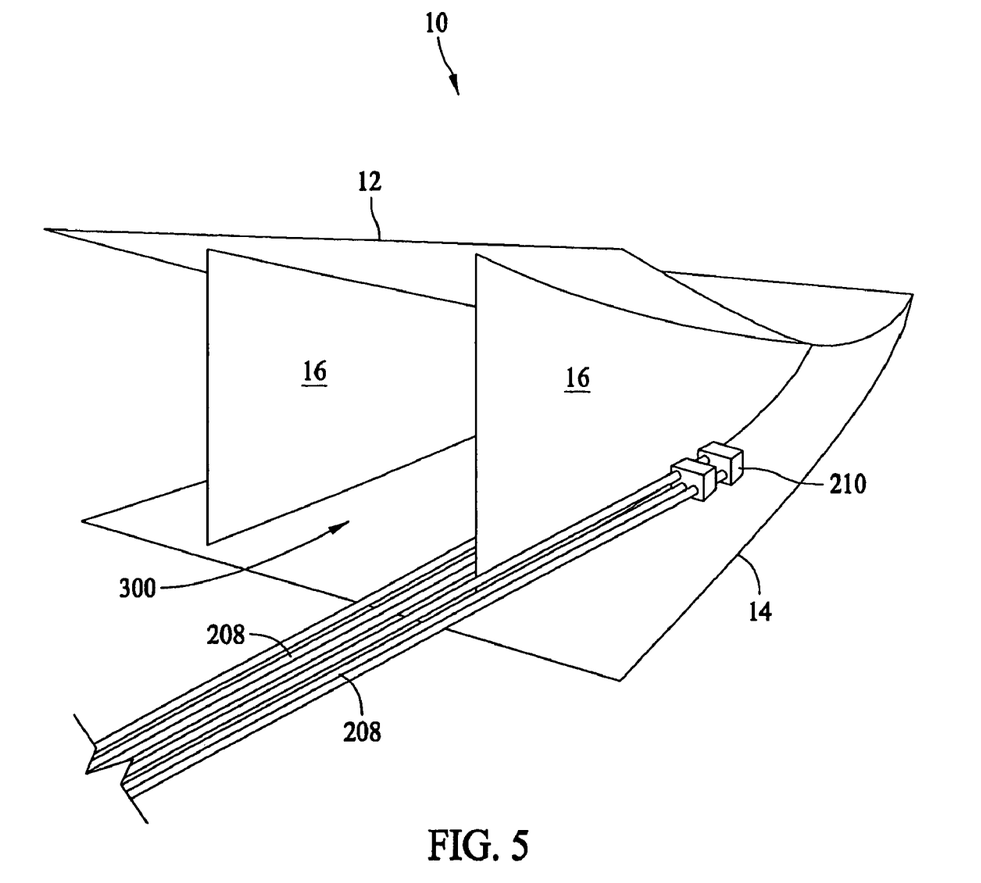
FIG. 5 is an illustration of rods of the mechanical device of FIG. 3 moving ultrasonic transducers within the wing component of FIG. 1 as part of an inspection process.

FIG. 5 illustrates an ultrasonic inspection being performed on wing component 10 utilizing mechanical device 200. One rod 208 is extending into cavity 300 and the other rod 208 is extending onto the other side of web component 16 for the inspection of web component 16. Water is injected into rods 208, which are hollow, at the end having handle 240 and the water runs through the hollow chamber within rods 208, and couples the transducer signals to the part being inspected. In one specific embodiment, seven channels of ultrasonic data are utilized to provide inspection of wing component 10. Each channel contains a transmit transducer and a receive transducer. The transmit transducers are on one side of web component 16 and the receive transducers are on the other side of web component 16. Electronics associated with inspection system 100 drive the transmit transducers and receive signals from the receive transducers through one or more coaxial cables also located inside rods 208. In this manner, the electronics of the through-transmission ultrasonic inspection system 100 send a pulse to the transmit transducers which generate an ultrasonic radio frequency (RF) that is coupled to web complement 16 by the water.

The RF signal is sent through web component 16, and received by the receive transducer on the other side of web component 16, the receive transducer also being water coupled to web component 16. The received signal is routed back to the electronics of the through-transmission ultrasonic inspection system 100 via another one are more coaxial cables inside rods 208. If there is a defect internal to web component 16, the RF signal reveals a change in magnitude and the electronics of through-transmission ultrasonic inspection system 100 sense this amplitude change.

Mechanical device 200 and ultrasonic inspection system 100 provides the capability to a quasi-manually inspect large recessed composite areas without the aid of motion control and the overhead associated with motion control. The air cylinders described herein are positioned on mechanical device 200 to minimize the user exerted force necessary to control movement of the transmit and receive transducers by countering the effects of gravity. The result is a manual inspection system that imposes a minimal impact to a human operator. The use of fast, multi-channel, ultrasonic electronics and positional feedback to the software of inspection system 100, provide the operator with the ability to see inspection results at rates in excess of seven inches/second. The result is that mechanical device 200 provides means for easy manual manipulation, respectable inspection speed, and area coverage, while still eliminating any need for motors, motion control hardware and software.

The above described inspection method utilizing mechanical device 200 is not limited to through-transmission ultrasonic inspection. Pulse echo and array ultrasonic inspection system components may also be mounted on the rods 208. As described above, in one pulse echo testing embodiment, the pulse echo components are mounted on a single rod 208. The combination of mechanical device 200 and through-transmission ultrasonic inspection system 100 is practical and the capabilities of mechanical device 200 result in an ultrasonic inspection system that is very portable. Such an inspection system provides flexible C-scanning areas which results in a testing and inspection capability for a large variety of components that, when fabricated, include one or more cavities.

In addition, such as system need not be limited to cavity scans but may be used to inspect any type of flat surface in a small amount of time.

The combination of mechanical device 200 and through-transmission ultrasonic inspection system 100 facilitates performing fast C-scan ultrasonic test inspection without robotic or gantry systems, and these inspections may be performed in areas that are extremely hard to access utilizing known C-scan ultrasonic testing and inspection systems. The system also provides quick feedback for a manufacturing process by providing a real-time display of an inspection area helping to ensure product quality.

While the invention has been described in terms of various specific embodiments, those skilled in the art will recognize that the invention can be practiced with modification within the spirit and scope of the claims.

What is claimed is:

1. An apparatus for the ultrasonic testing of internal areas of prefabricated composite assemblies, said apparatus comprising:
    at least one receive transducer;
    at least one transmit transducer;
    a vertical member;
    a support member slidably attached to said vertical member;
    a pair of substantially parallel hollow rods, each said rod comprising a transducer attachment end, said at least one receive transducer attached to said transducer attachment end of a first said rod, said at least one transmit transducer attached to said transducer attachment end of a second said rod, said rods slidably attached to said support member and manually movable with respect to a composite assembly to be tested; and
    an ultrasonic testing system coupled to said at least one receive transducer through a first of said rods, said ultrasonic testing system coupled to said at least one transmit transducer through a second of said rods.

2. An apparatus according to claim 1 wherein said vertical member comprises at least one groove formed therein, and said support member comprises at least one wheel attached thereto, said at least one wheel configured to engage said at least one groove to provide slidable attachment of said support member to said vertical member.

3. An apparatus according to claim 1 further comprising at least one air cylinder, said at least one air cylinder attached to said support bracket and said vertical member to provide operator assisted movement of said support bracket with respect to said vertical member.

4. An apparatus according to claim 1 further comprising a plurality of magnets, said magnets attached to said rods and configured to maintain an alignment between said at least one receive transducer and said at least one transmit transducer.

5. An apparatus according to claim 1 further comprising at least one encoder attached to said vertical member, said at least one encoder configured to monitor at least one of back and forth movement and up and down movement of said transmit and receive transducers.

6. An apparatus according to claim 1 wherein said rods are hollow and configured to pass a fluid stream to said transmit and receive transducers, the fluid stream coupling from said transmit transducers and said receive transducers to the composite assembly to be tested.

7. An apparatus according to claim 1 wherein said rods comprise a handle at an end opposite said transducer attachment end, said handle used to manually manipulate said transmit and receive transducers.

8. An apparatus according to claim 1 wherein said ultrasonic testing system comprises at least one of a through-transmission ultrasonic inspection system, a pulse echo ultrasonic inspection system, and an array ultrasonic inspection system.

9. An apparatus according to claim 1 wherein said ultrasonic testing system configured to map the received ultrasonic test data to an X and Y C-scan image for user review.

10. An apparatus according to claim 1 further comprising a portable horizontal base, said vertical member attached to said portable horizontal base.

11. A method for operator controlled ultrasonic inspection of prefabricated composite assemblies, said method comprising:
    engaging the assembly to be inspected with transmit and receive transducers, the transmit and receive transducers mounted opposite one another on substantially parallel, hollow, rods, the portion of the assembly to be inspected in the space between the transmit transducers and the receive transducers;
    providing a fluid flow within the rods, the fluid flow coupling the transmit transducers and the receive transducers to the assembly being inspected;
    outputting ultrasonic inspection signals from the transmit transducers;
    receiving the ultrasonic inspection signals at the receive transducers;
    providing for planar, operator assisted movement of the rods during the outputting and receiving steps; and
    analyzing the signals received at the receive transducers to determine a condition of the assembly being inspected.

12. A method according to claim 11 wherein providing for planar movement of the rods further comprises configuring one or more encoders to monitor back and forth movement, and up and down movement, of the transmit and receive transducers.

13. A method according to claim 11 wherein providing for planar movement of the rods comprises:
    attaching the rods to a support member that is slidably engaged to a vertical member; and
    configuring an air cylinder to provide operator assisted movement of said support bracket with respect to the vertical member.

14. A method according to claim 11 wherein providing for planar and movement of the rods comprises using a handle to manually manipulate the transmit and receive transducers, the handle attached to the rods at an end opposite the transducer attachment end.

15. A device enabling operator assisted ultrasonic inspection of composite assemblies, said device comprising:
    a vertical member;
    a support bracket slidably attached to said vertical member;
    an air cylinder attached to said support bracket and said vertical member, said air cylinder configured for operator assisted movement of said support bracket with respect to said vertical member;
    a pair of rods slidably attached to said support bracket and substantially perpendicular to said vertical member, said rods manually movable with respect to said support bracket, said rods each comprising a transducer attachment end; and
    transmit and receive transducers mounted to respective said transducer attachment ends, said transducers oriented such that a composite assembly may be inserted into a space between said transmit transducers and said receive transducers and between said rods.

16. A device according to claim 15 wherein said rods are configured with a bore therethrough, said rods further configured to pass a fluid to said transmit and receive transducers, the fluid coupling said transmit transducers to the composite assembly and coupling the composite assembly to said receive transducers.

17. A device according to claim 15 further comprising at least one encoder to monitor movement of said transmit and receive transducers, said encoder outputting signals indicative of the movement of said rods with respect to said support bracket.

18. A device according to claim 15 further comprising at least one encoder to monitor movement of said transmit and receive transducers, said encoder outputting signals indicative of the movement of said support member with respect to said vertical member.

19. A device according to claim 15 further comprising a plurality of magnets, said magnets attached to said rods such that an alignment between said receive transducers and said transmit transducers is maintained.

20. A device according to claim 15 wherein said rods comprise a handle at an end opposite said transducer attachment end, said handle configured for use by an operator to manually manipulate said rods to adjust a position of said transmit and receive transducers.

21. An apparatus for pulse echo testing of prefabricated composite assemblies, said apparatus comprising:
   at least one receive transducer;
   at least one transmit transducer;
   a vertical member;
   a support member slidably attached to said vertical member;
   a rod comprising a transducer attachment end, said at least one receive transducer and said at least one transmit transducer attached to said transducer attachment end of said rod, said rod slidably attached to said support member and manually movable with respect to a composite assembly to be tested; and
   an ultrasonic testing system coupled to said at least one receive transducer and said at least one transmit transducer through said rod.

22. An apparatus according to claim 21 further comprising at least one air cylinder, said at least one air cylinder attached to said support member and said vertical member to provide operator assisted movement of said support member with respect to said vertical member.

23. An apparatus according to claim 21 further comprising at least one encoder attached to said vertical member, said at least one encoder configured to monitor at least one of back and forth movement and up and down movement of said transmit and receive transducers.

24. An apparatus according to claim 21 wherein said rod is hollow and configured to pass a fluid stream to said transmit and receive transducers, the fluid stream coupling said transmit transducers and said receive transducers to the composite assembly to be tested.

25. An apparatus according to claim 21 wherein said rod comprises a handle at an end opposite said transducer attachment end, said handle used to manually manipulate said transmit and receive transducers with respect to the assembly to be tested.

* * * * *